US009730789B2

(12) United States Patent
Kartush et al.

(10) Patent No.: US 9,730,789 B2
(45) Date of Patent: Aug. 15, 2017

(54) OSSICULAR PROSTHESIS HAVING A LONGITUDINALLY PERFORATED BIGHT

(71) Applicant: HEINZ KURZ GMBH MEDIZINTECHNIK, Dusslingen (DE)

(72) Inventors: Jack M. Kartush, Bloomfield Hills, MI (US); Uwe Steinhardt, Hirrlingen (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 145 days.

(21) Appl. No.: 14/670,579

(22) Filed: Mar. 27, 2015

(65) Prior Publication Data
US 2015/0272728 A1 Oct. 1, 2015

(30) Foreign Application Priority Data
Mar. 31, 2014 (DE) .................... 20 2014 101 511 U

(51) Int. Cl.
*A61F 2/18* (2006.01)
*H04R 25/00* (2006.01)

(52) U.S. Cl.
CPC .......... *A61F 2/18* (2013.01); *A61F 2002/183* (2013.01); *H04R 25/606* (2013.01)

(58) Field of Classification Search
CPC .... A61F 2/18; A61F 2002/183; H04R 25/606
See application file for complete search history.

(56) References Cited

U.S. PATENT DOCUMENTS

| 3,711,869 A | 1/1973 | Shea, Jr. |
| 3,931,648 A | 1/1976 | Shea, Jr. |

(Continued)

FOREIGN PATENT DOCUMENTS

| CN | 1382426 | 12/2002 |
| CN | 1937970 | 3/2007 |

(Continued)

OTHER PUBLICATIONS

Alexander M Huber et al: "Stapes Prosthesis Attachment: The Effect of Crimping on Sound Transfer in Otosclerosis Surgery" Laryngoscope 113, May 2003, pp. 853-858.

(Continued)

*Primary Examiner* — Katrina Stransky
*Assistant Examiner* — Daniel Bissing
(74) *Attorney, Agent, or Firm* — Michael J. Striker

(57) ABSTRACT

A passive ossicular prosthesis has a sound-conducting prosthesis body with a first coupling element for mechanical connection to the incus, malleus, or an actuator end piece of an active hearing aid at one end. The bight is made of a strip-shaped metallic material, partially open toward the outside via a gap-type opening and is intraoperatively crimped in the middle ear for permanent attachment. There is a second coupling element at the other end of the prosthesis body for connection to a further component of the ossicular chain or directly to the inner ear. The bight includes elongated perforations with longitudinal axes extending, in the implanted state, along a curved trajectory at a right angle or slant relative to an axis parallel to the longitudinal axis (a) of the enclosed object to reduce spring action and stiffness and markedly reduce the force to be applied for the crimping.

13 Claims, 3 Drawing Sheets

(56) References Cited

U.S. PATENT DOCUMENTS

| | | |
|---|---|---|
| 5,514,177 A | 5/1996 | Kurz et al. |
| 6,554,861 B2 | 4/2003 | Knox et al. |
| 7,238,202 B2 | 7/2007 | Steinhardt et al. |
| 7,871,439 B2 | 1/2011 | Awengen et al. |
| 8,906,090 B2 | 12/2014 | Steinhardt et al. |
| 2005/0027357 A1 | 2/2005 | Steinhardt et al. |
| 2007/0055372 A1 | 3/2007 | Prescott et al. |
| 2011/0178364 A1* | 7/2011 | Ball .................. A61F 2/18 600/25 |
| 2012/0016180 A1 | 1/2012 | Abel et al. |
| 2012/0078368 A1 | 3/2012 | Lenarz et al. |
| 2013/0053957 A1* | 2/2013 | Scheurer .............. A61F 2/18 623/10 |

FOREIGN PATENT DOCUMENTS

| | | |
|---|---|---|
| CN | 103442322 | 12/2013 |
| DE | 102007008851 | 6/2008 |
| DE | 202014100093 | 3/2014 |
| EP | 1706071 | 10/2006 |
| EP | 1759662 | 3/2007 |
| EP | 2385808 | 11/2011 |
| EP | 2583639 | 4/2013 |
| WO | WO 02/069850 | 9/2002 |

OTHER PUBLICATIONS

Pingling Kwok et al: "Stapes Surgery: How Precisely Do Different Prostheses Attach to the Long Process of the Incus With . . . ?" Otology & Neurotology 23, 2002, pp. 289-295.

Marco Fontana et al: "A Scanning Electron Microscopic Study of Crimping of Stapedial Prostheses" Auris Nasus Larynx 39, 2012, pp. 461-468.

Michael H. Fritsch et al: "Histopry of Otology Phylogeny of the Stapes Prostheses" Otology & Neurotology 29, 2008, pp. 407-415.

Textbook "Middle Ear Surgery" by Hildmann and Sudhoff, Published by Springer-Verlag Berlin, Heidelberg, ISBN: 978-3-540-22201-9, 2206, p. 117.

* cited by examiner

OSSICULAR PROSTHESIS HAVING A
LONGITUDINALLY PERFORATED BIGHT

CROSS-REFERENCE TO A RELATED
APPLICATION

The invention described and claimed hereinbelow is also described in German Patent Application DE 20 2014 101511.6, filed on Mar. 31, 2014. The German Patent Application, the subject matters of which is incorporated herein by reference, provides the basis for a claim of priority of invention under 35 U.S.C. 119(a)-(d).

BACKGROUND OF THE INVENTION

The invention relates to passive ossicular prosthesis designed to replace or bridge at least one component of the human ossicular chain. The ossicular prosthesis comprises an elongated, sound-conducting prosthesis body, which at one end has a first coupling element designed in the form of a bight. The bight is made of a strip-shaped metallic material, is partially open toward the outside via a gap-type opening and encloses the component of the ossicular chain or the actuator end piece for mechanical connection to the long process of incus (="incus"), the manubrium of malleus ("malleus"), or an elongated actuator end piece of an active hearing aid. Post-operatively, the bight encloses the long process of incus, the manubrium of malleus, or the actuator end piece in a non-positive manner and, intraoperatively, can be deformed, using crimping tongs, in the middle ear for the fixation and permanent attachment of the first coupling element to the long process of incus, the manubrium of malleus, or the actuator end piece. The prosthesis body comprises, at the other end thereof, a second coupling element for mechanical connection to a further component or parts of a component of the ossicular chain or directly to the inner ear.

A known passive ossicular prosthesis is described and shown in DE 20 2014 100 093 U1. Therein, the special problems associated with the intraoperative crimping of bight-shaped parts of a first coupling element are described, in particular, although merely in conjunction with the bridging of parts or components of the ossicular chain, but not for coupling the passive prosthesis to an actuator end piece of an active hearing aid.

Similar known passive ossicular prostheses, which are typically designed as stapes prostheses, are described in U.S. Pat. No. 3,711,869 and U.S. Pat. No. 3,931,648. Therein, the first coupling element is not designed as a bight, but rather as a clip that is intended to be self-closing and self-retaining via the spring properties thereof, and is therefore not crimped, as is the case with the bight of a prosthesis of the type in question.

In the case of the ossicular prostheses known from EP 2 385 808 B1 or EP 2 583 639 A1, however, a first coupling element is made of a strip-shaped, flexible material and is provided with slits parallel to the longitudinal axis of the component of the ossicular chain to be enclosed. However, the geometric design of the coupling element used therein is not bight-shaped, but rather is designed as a loop that is intraoperatively inserted, via the free end thereof, into an eyelet intended therefor on the prosthesis body. An attachment step, which is comparable to the crimping procedure used to intraoperatively affix the bight according to the initially cited document DE 20 2014 100 093 U1, is not carried out with these known prostheses.

Ossicular prostheses in which the first coupling element is actually designed as a bight are shown and described in U.S. Pat. No. 6,554,861 and DE 10 2007 008 851 B3, for example. Therein, however, in contrast to the initially mentioned prostheses of the type in question, the bight is not made of strip-shaped metallic material, but rather of round wire material. The crimping procedure for same is therefore considerably different than for the prostheses of the type in question in terms of the intraoperative attachment of the bight.

The human middle ear comprising the ossicles thereof has the function of transmitting the sound waves impacting the tympanic membrane via the external auditory meatus to the inner ear, which is filled with fluid. The three ossicles are the hammer (lat. malleus), which is attached to the tympanic membrane, the stirrup (lat. stapes), which is connected via the footplate (lat. basis stapedis) thereof to the inner ear and the anvil (lat. incus), which is located between the hammer and the stapes and is hingedly connected thereto. For example, otosclerosis is a disease of the human petrosal bone (=bone in which the entire ear is seated), in which inflammation-like bone remodeling processes can result in fixation of the stapes, which normally swings freely.

As a result, the sound signal is transmitted incompletely or not at all via the ossicular chain to the inner ear, thereby resulting in hearing loss.

Ossicular prostheses are used, in general, to improve sound transmission in patients having different pathologies. Ossicular prostheses are used to improve or merely enable the transfer of sound from the tympanic membrane to the inner ear in cases in which the ossicles of the human middle ear are missing or damaged, either entirely or partially. The passive ossicular prosthesis has two ends. Depending on the specific circumstances, one end of the ossicular prosthesis is attached to the tympanic membrane, an ossicles, or the actuator end piece of an active electronic hearing aid and the other end of the ossicular prosthesis is attached, e.g., to the stapes of the human ossicular chain, or is inserted directly into the inner ear.

Three types of ossicular prostheses that are used particularly frequently are stapes prostheses, partial prostheses and total prostheses. Stapes prostheses are usually fixed on the long process of incus and extend via a piston into the inner ear or are seated, with the piston, on a piece of tissue that seals the inner ear. Partial prostheses typically bear via a top plate against the tympanic membrane and establish a connection to the head of the stapes. Total prostheses connect the tympanic membrane to the base of stapes.

In addition, a distinction is generally made between passive ossicular prostheses and active hearing implants having electronic amplification elements, which are operated via an external energy part. The initially defined ossicular prosthesis of the type in question is a passive prosthesis in which a coupling element is provided at the upper end of the prosthesis body and is crimped with the long process of incus (="incus"), the manubrium of malleus ("malleus"), or an actuator end piece of an active hearing aid.

The methods and problems associated with the attachment of such ossicular prostheses having a bight-shaped coupling element are extensively described in the scientific literature.

Stapes prostheses designed specifically for connection to the incus, which comprise, as the first coupling element, a bight, a loop, or a clip for crimping around the incus are extensively described in respect of their geometric design, the details of their coupling to the incus, and in respect of their mode of operation in the following, for example, in Fritsch, et al., "History of Otology: Phylogeny of the Stapes Prosthesis", Otology & Neurotology, 29: 407-415, 2008; in Fontana, et al., "A scanning electron microscopic study of crimping of stapedial prostheses", Auris Nasus Larynx 39 (2012) 461-468; in Kwok, et al., "Stapes Surgery: How Precisely Do Different Prostheses Attach to the Long Process of Incus with Different Instruments and Different Surgeons?", Otology & Neurotology, 23: 289-295, 2002; and in a textbook "Middle Ear Surgery" by Hildmann and Sudhoff, published by Springer-Verlag Berlin Heidelberg, ISBN: 978-3-540-22201-9, 2006 (see in particular, page 117). In addition, in the article by Huber, et al., "Stapes Prosthesis Attachment: The Effect of Crimping on Sound Transfer in Otosclerosis Surgery", Laryngoscope 113: May 2003, there is a detailed discussion of the problems that can result from the current crimping techniques used with such stapes prostheses.

The known crimp stapes prostheses, which usually comprise a piston for coupling to the inner ear at the lower end of the prostheses, are typically applied on the long process of incus, for example, by crimping or alligator pincers. This application comprises simply placing or laying the bight on the incus. In the next step, the bight is closed with the pincers. This closing process is still considered to be the most difficult part of the middle ear operation, namely, because the closing process itself can cause the piston to be moved medially into the inner ear. These movements can result in relatively minor but also serious inner ear damage, which can have a negative effect on the patient's postoperative state of health.

Since the incus is basically never round or oval, due to anatomical variation, but rather typically has a highly complex cross-section, it is advantageous when the bight has the least possible memory spring effect. Therefore, when the bight is closed with the pincers, the surgeon would like to achieve the most gentle, soft, and permanent plastic deformation possible without any subsequent recoil.

The disadvantage of the initially described ossicular prosthesis of the type in question, which is known from DE 20 2014 100 093 U1, for example, is the ever-present tendency for the metallic material of the bight to recoil during crimping due to the aforementioned mechanical memory spring effect, which becomes apparent as the strip material bending. The intrinsic stiffness of the material also causes problems, however, in respect of a deformation of the coupling element in the intraoperative processing that is as precise and permanent as possible.

The problem addressed by the present invention is that of improving a passive ossicular prosthesis of the initially described type in question using the simplest technical means possible and as cost-effectively as possible such that said ossicular prosthesis can be produced using particularly simple and economical process engineering, and in which the above-described mechanical memory spring effects occur not at all or are markedly reduced, wherein the intrinsic stiffness of the material should also be reduced by the greatest extent possible.

SUMMARY OF THE INVENTION

The present invention overcomes the shortcomings of known arts, such as those mentioned above.

To that end, the invention provides an ossicular prostheses with a bight made of strip-shaped metallic material comprising a plurality of elongated perforations, the longitudinal axes of which each extend, in the implanted state of the ossicular prosthesis, along a curved trajectory at a right angle or at a slant relative to an axis that is parallel to the longitudinal axis of the long process of incus, the manubrium of malleus, or the actuator end piece.

In an (imaginary) flat state of the bight, which is curved in the implanted state, the elongated perforations therefore extend in the longitudinal direction of the flat, strip-shaped material of the bight or, at the least, at an acute angle relative to the longitudinal direction of the strip such that, in the implanted state of the ossicular prosthesis, each of the perforations extends along a curved trajectory at a right angle or at a slant relative to the longitudinal axis of the component of the ossicular chain or the elongated actuator end piece to be enclosed.

In this manner, the spring action of the flat strip material of the bight can be substantially reduced and the force that must be applied for the crimping is markedly less, namely by approximately 50%.

In contrast to the ossicular prosthesis according to the aforementioned document EP 2 385 808 B1, which has slits extending parallel to the longitudinal axis of the component of the ossicular chain to be enclosed, the perforations of the prosthesis according to the invention each extend along a curved trajectory at a right angle or at a slant relative to an axis extending parallel to the longitudinal axis of the part to be enclosed, i.e., substantially parallel to the shank of the prosthesis, while the perforations in the loop according to EP 2 385 808 B1 extend transversely thereto. In addition, the prosthesis according to the invention having the open bight does not need the eyelet, which accommodates the free end of the loop, or any other such mechanism, into which the loop must be inserted.

The bight having the elongated perforations described above according to the invention also has the advantage, inter alia, in comparison to the loop having the transverse perforations according to EP 2 385 808 B1, that the bight does not bend sharply at the weak point and, therefore, can be placed around the long process of incus, the manubrium of malleus or the elongated actuator end piece so as to have a rounder shape.

This results in a reduction in the force that the surgeon must apply and, therefore, in a reduction of the risk that the long process of incus or the manubrium of malleus will be traumatized by crimping that is too forceful. Another result, however, is a reduction in the aforementioned mechanical memory effect and, therefore, improved coupling of the ossicular prosthesis from an acoustic perspective.

Due to the elongated perforations, the surgeon can also basically mold the bight to the incus using a fine hook and thereby achieve a contact surface that is as secure as possible. This contact surface subsequently ensures that reliable acoustic signal transmission takes place.

If a revision operation is unexpectedly required and the prosthesis must be removed from the middle ear, the perforations are of considerable advantage once more, since the prosthesis can be gripped in the perforations by means of a fine hook and can therefore be very easily removed from the incus.

In practical use, the elongated perforations can be formed in the bight of the first coupling element in a particularly precise and uncomplicated manner by laser cutting.

A class of embodiments of the ossicular prosthesis according to the invention that is particularly easy to manufacture is characterized in that the elongated perforations in the strip-shaped metallic material have through-slits that are straight in the flat state of said strip-shaped metallic material. Once the bight lies against the incus, the mucous membrane that covers the incus can grow through the perforations and thereby also produce an acoustically permanent connection over the mid-term. A further advantage is that, in the event that the intraoperative coupling is inadequate, the prosthesis can be fixedly bonded through the perforations by means of adhesive or cement.

In simple developments of these embodiments, the through-slits have two parallel lateral borders in the longitudinal direction thereof and have consistent slit widths along the longitudinal extension. The slits therefore have a substantially elongated rectangular shape.

As an alternative, however, in other developments, the through-slits can taper in the longitudinal direction thereof and can have slit widths that continuously diminish in the tapering direction.

An alternative class of embodiments of the invention is characterized in that the elongated perforations have through-slits that extend on the strip-shaped metallic material in a serpentine or zigzag manner in the flat state of said strip-shaped metallic material.

In a third class of embodiments of the ossicular prosthesis according to the invention, the elongated perforations have through-slits that extend on the strip-shaped metallic material in a meandering manner in the flat state of said strip-shaped metallic material. In this manner, it is possible, inter alia, for the width of the strip to taper, if this should be necessary for reasons related to the patient's anatomy.

In other embodiments of the ossicular prosthesis according to the invention the bight comprises at least two parallel rows of elongated perforations, which are spaced apart, one behind the other, in the direction of the respective longitudinal axes thereof. This widening of the slit structure considerably reduces pressure peaks that can act on the tissue and the bones.

Preferably, all the elongated perforations have the same size. The uniform size of the perforations results in a more uniform stiffness of the first coupling element.

In addition or as an alternative thereto, the elongated perforations are disposed in a row so as to be staggered in the longitudinal direction relative to the elongated perforations of an adjacent row. As a result, no sharp bends form, in particular during the intraoperative processing of the strip-shaped metallic material, since the resistive force remains constant.

A class of embodiments of the invention that is particularly cost-effective to manufacture is characterized in that the bight has an insertion projection at a free end of the strip-shaped metallic material, at the gap-type opening, which insertion projection facilitates the bending or compression of the bight by crimping tongs.

Preferably, the insertion projection of the bight is offset relative to the curved parts thereof, which enclose the long process of incus, the manubrium of malleus or the actuator end piece in the implanted state of the ossicular prosthesis, such that the insertion projection extends away from the longitudinal axis of the long process of incus, the manubrium of malleus, or the actuator end piece. The surgeon can grasp the bight at this point with a fine hook and basically pull said blight around the incus such that the bight rests thereon as directly as possible.

In embodiments of the ossicular prosthesis according to the invention, the second coupling element is designed as a piston for engagement in the inner ear appear to be preferable for practical use.

Preferably, the prosthesis body comprises at least one joint, in particular a ball joint. This is advantageous in terms of particularly high postsurgical mobility of the prosthesis. Developments also are possible in which a plurality of mutually adjacent, further rotary elements is provided, preferably a ball joint chain. Once the prosthesis has been surgically implanted in the middle ear and the tympanic membrane has been closed, the recovery phase begins. Scars form during this period that produce unforeseeable forces which can cause the prosthesis to move out of localized position thereof.

The ossicular prosthesis, according to the invention, or parts thereof may be made of titanium and/or gold and/or tantalum and/or steel, and/or an alloy of said metals. It is known that titanium, in particular, in addition to being stiff and having excellent sound-conducting properties, also exhibits excellent biocompatibility with the human ear.

In terms of the postsurgical position adjustment described above, embodiments of the present invention are advantageous in which the ossicular prosthesis or parts thereof are composed of a material having memory effect or superelastic properties, Nitinol in particular, as is known per se, for example, from WO 02/069850 A1 or U.S. Pat. No. 6,554,861 B2.

As an alternative or in addition thereto, in further embodiments, parts of the ossicular prosthesis according to the present invention may be composed of a ceramic material.

Embodiments of the present invention also are possible, however, in which the entire prosthesis or parts thereof are made of biocompatible plastics, particularly silicone, polytetrafluoroethylene (PTFE), or fibrous composite materials. With these materials, postsurgical rejection reactions may also be prevented in most cases.

According to a particularly preferred embodiment of the ossicular prosthesis according to the present invention, the mass distribution of the individual parts of the prosthesis is calculated depending on a desired, specifiable frequency response of sound conduction in the middle ear. This allows the sound propagation properties to be tuned to a certain extent using a custom-made ossicular prosthesis without a great deal of additional technical complexity. Frequency adaptation for improved sound conduction in the middle ear is broadly described, for example, in EP 1 706 071 B1 or U.S. Pat. No. 7,871,439 B2.

In special embodiments, such "mechanical tuning" may be achieved, for example, by fastening at least one additional mass to a part of the ossicular chain or the prosthesis depending on a desired, specifiable frequency response of sound conduction in the middle ear. The additional mass is fastened to a part of the ossicular chain or the prosthesis using a clip. The additional mass and/or clip also may be coated with a biologically active coating.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
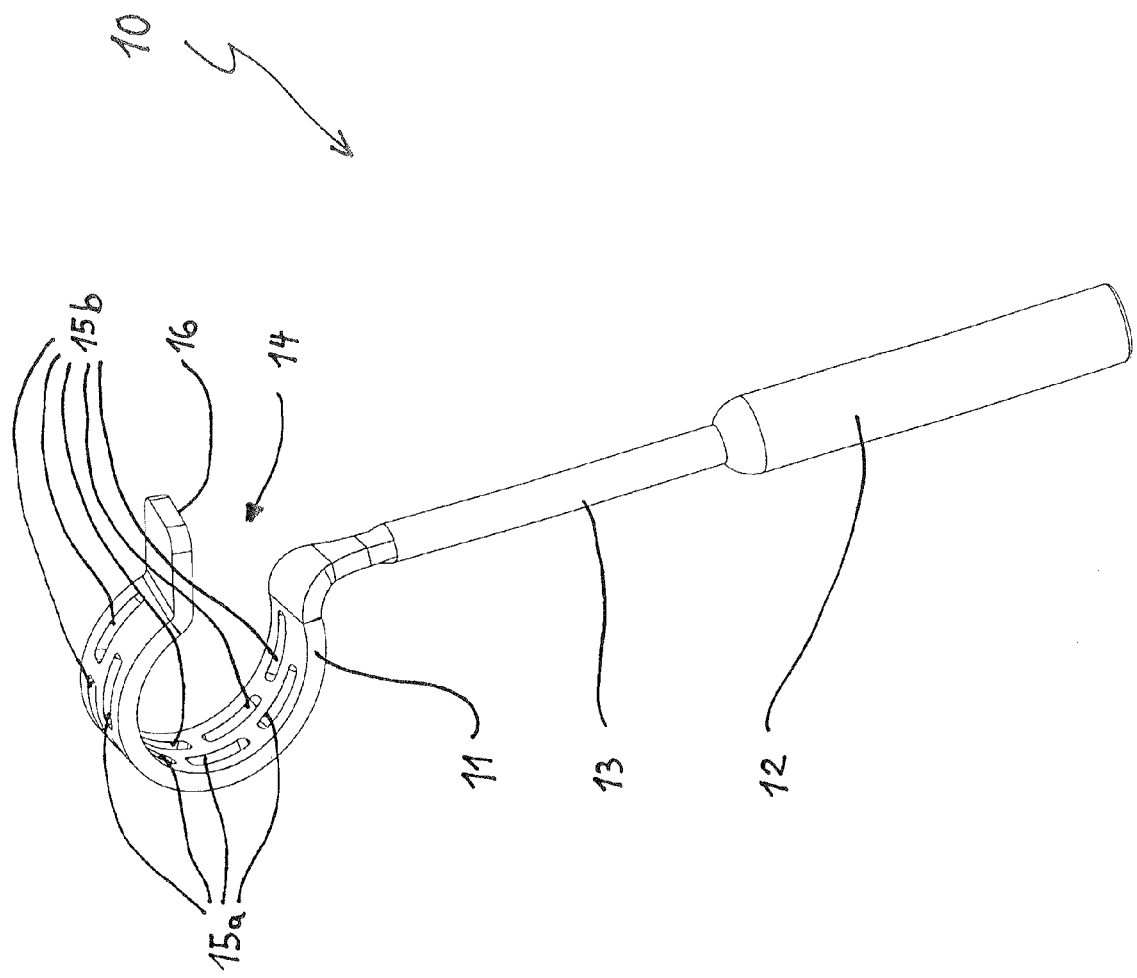
FIG. 1: presents a schematic spatial depiction an embodiment of the ossicular prosthesis according to the invention standing upright and tilted to the side.

FIG. 1 depicts an ossicular prosthesis 10 according to the invention, which comprises a shank-shaped, elongated, sound-conducting prosthesis body 13, which comprises a first coupling element 11 at one end. The first coupling element 11 is designed in the form of a bight made of a strip-shaped metallic material. The bite encloses the desired component of the ossicular chain or the actuator end piece and is partially open toward the outside via a gap-type opening 14 for mechanical connection to the long process of incus (="incus"), the manubrium of malleus ("malleus"), or an elongated actuator end piece of an active hearing aid. The bight post-operatively encloses the long process of incus, the manubrium of malleus, or the actuator end piece in a non-positive manner.

Figure 2:
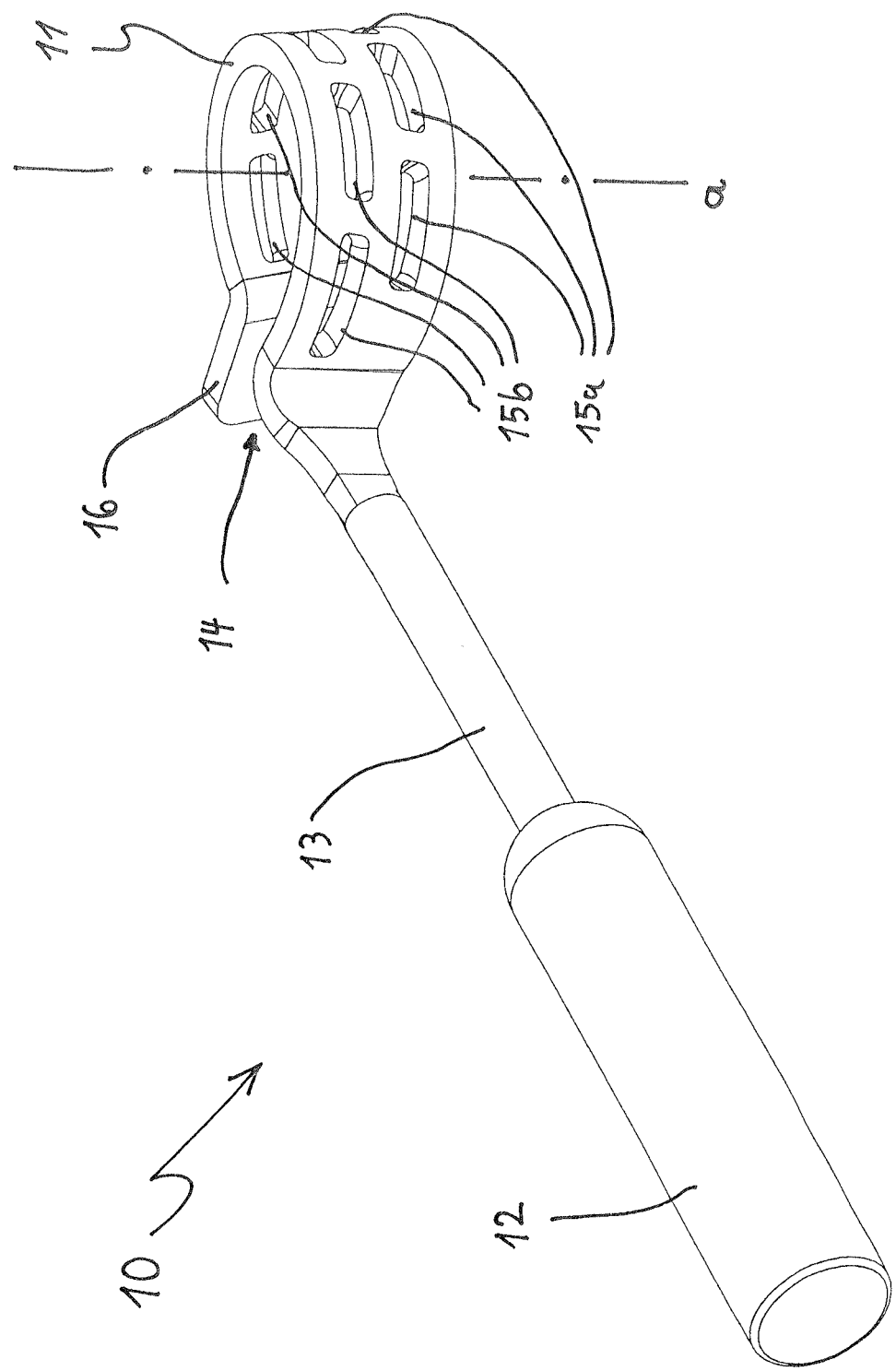
FIG. 2 shows the embodiment according to FIG. 1, lying down, as viewed from the back side.
Figure 3:
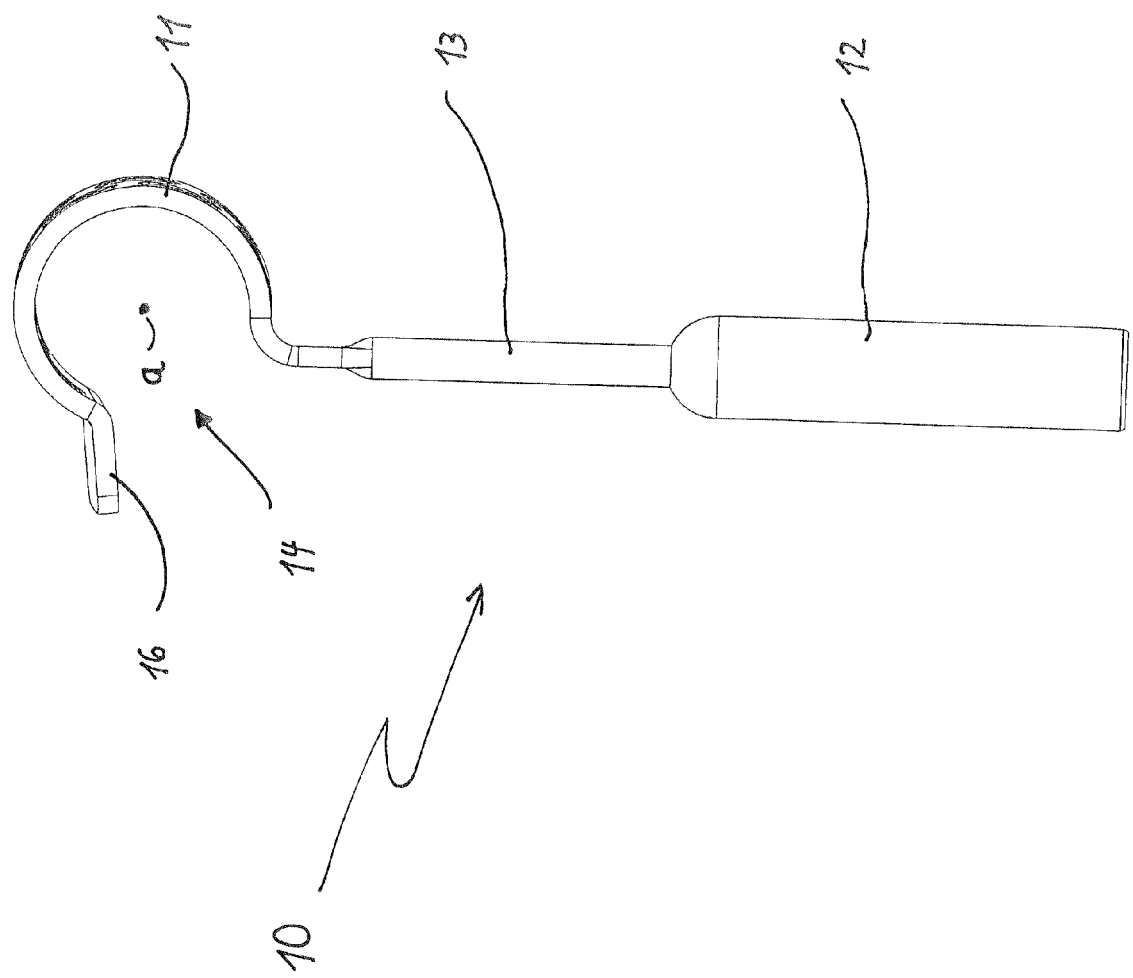
FIG. 3 shows the embodiment according to FIG. 1 in a side view as seen in the direction parallel to a position of a longitudinal axis of the long process of incus, the manubrium of malleus, or the actuator end piece, in the implanted state of the prosthesis.

The component of the ossicular chain or the actuator end piece to be enclosed by the bight is not shown in the drawings. Merely shown, in a graphic depiction, is the longitudinal axis a of the long process of incus, the manubrium of malleus, or the actuator end piece to be enclosed, in the position thereof relative to the ossicular prosthesis 10 in the state thereof implanted in the middle ear, as a dash-dotted line in FIG. 2 and as a point in FIG. 3, as an axis extending perpendicularly through the plane of the drawing.

Located at the other end of the prosthesis body 13 is a second coupling element 12, as shown. Second coupling element 12 can be embodied in diverse geometric shapes for mechanical connection to a further component or parts of a component of the ossicular chain or as shown, as a piston for insertion directly into the inner ear.

The ossicular prosthesis 10 is characterized in that the bight, which is made of a strip-shaped metallic material, comprises a plurality of elongated perforations 15a, 15b, the longitudinal axes of which each extend (in the implanted state of the ossicular prosthesis 10) along a curved trajectory at a right angle or at a slant relative to an axis that is parallel to the longitudinal axis a of the long process of incus, the manubrium of malleus or the actuator end piece enclosed by the bight. The elongated perforations 15a, 15b in the bight of the first coupling element 11 are produced by laser cutting.

In the ossicular prosthesis 10, the first coupling element 11 is configured such that the bight has an insertion projection 16 at a free end of the strip-shaped metallic material, at the gap-type opening 14. The insertion projection 16 facilitates the bending or compression of the bight by use of crimping tongs. The insertion projection 16 of the bight is offset relative to the curved parts thereof, which enclose the long process of incus, the manubrium of malleus, or the actuator end piece in the implanted state of the ossicular prosthesis 10, such that said insertion projection extends away from the longitudinal axis a of the long process of incus, the manubrium of malleus, or the actuator end piece.

In the embodiment shown, the elongated perforations 15a, 15b in the strip-shaped, metallic material have through-slits, which are straight in the flat state of the strip-shaped, metallic material and which have two parallel lateral borders in the longitudinal direction thereof and have consistent slit widths along the longitudinal extension.

As an alternative thereto, the through-slits may taper in the longitudinal direction thereof and have slit widths that continuously diminish.

In other embodiments, the elongated perforations in the strip-shaped metallic material may have through-slits that extend in a serpentine or zigzag or meandering manner in the flat state of said strip-shaped metallic material.

The bight as shown comprises two parallel rows of elongated perforations 15a, 15b, which are spaced apart, one behind the other, in the direction of the respective longitudinal axes thereof and all have the same size. Also as shown, the elongated perforations 15a, 15b are disposed in a row in the longitudinal direction so as to be staggered relative to the elongated perforations 15a, 15b of an adjacent row. In other embodiments of the invention, it is possible to provide more than two rows of parallel, elongated perforations.

For that matter, in other embodiments of the invention, prosthesis body comprises at least one joint, in particular, a ball joint.

The mass distribution of the individual parts of an ossicular prosthesis according to the invention is calculated depending on a desired, specifiable frequency response of sound conduction in the middle ear such that it is possible to tune the sound propagation properties in an individualized manner. This can be achieved by way of trimming masses that can be clipped to the ossicular prosthesis.

The ossicular prosthesis 10 as shown is made entirely or partially of a material having memory effect and/or having superelastic properties, such as Nitinol. The invention, however, is not limited to being made with Nitinol but may be made by other metals or metal composites.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A passive ossicular prosthesis designed to replace or bridge at least one component of a human ossicular chain, comprising:
    a sound-conducting prosthesis body with a first coupling element designed in a form of a bight at one end and a second coupling element at another end;
    wherein the bight is made of a strip-shaped metallic material, is partially open toward an outside via a gap-type opening, is configured to enclose at least one of: the at least one component of the human ossicular chain, an actuator end piece for mechanical connection to the long process of incus, the manubrium of malleus, and an elongated actuator end piece of an active hearing aid, post-operatively encloses at least one of: the long process of incus, the manubrium of malleus and the actuator end piece in a non-positive manner and, intraoperatively is deformable using crimping tongs in the middle ear for fixation and permanent attachment of the first coupling element to at least one of: the long process of incus, the manubrium of malleus, or the actuator end piece;
    wherein the second coupling element is configured for mechanical connection to a further component or parts of a component of the ossicular chain or directly to the inner ear; and
    wherein the bight made of strip-shaped metallic material comprises a plurality of elongated perforations, longitudinal axes of which are configured to extend, in an implanted state of the ossicular prosthesis, along a curved trajectory at a right angle or at a slant relative to an axis that is parallel to at least one of: a longitudinal axis of the long process of incus, the manubrium of malleus or the actuator end piece.

2. The ossicular prosthesis according to claim 1, wherein the elongated perforations in the strip-shaped metallic material have through-slits that are straight in the flat state of said strip-shaped metallic material.

3. The ossicular prosthesis according to claim 2, wherein the through-slits have two parallel lateral borders in the longitudinal direction thereof and have consistent slit widths along the longitudinal extension.

4. The ossicular prosthesis according to claim 1, wherein the bight comprises at least two parallel rows of elongated perforations that are spaced apart, one behind the other, in the direction of the respective longitudinal axes thereof.

5. The ossicular prosthesis according to claim 4, wherein the elongated perforations all have the same size.

6. The ossicular prosthesis according to claim 4, wherein the elongated perforations are disposed in a row to be staggered in the longitudinal direction relative to the elongated perforations of an adjacent row.

7. The ossicular prosthesis according to claim 1, wherein the bight has an insertion projection at at least one of: a free end of the strip-shaped metallic material, and at the gap-type opening that facilitates the bending or compression of the bight by use of crimping tongs.

8. The ossicular prosthesis according to claim 7, wherein the insertion projection of the bight is offset relative to the curved parts thereof, which curved parts are configured to enclose at least one of: the long process of incus, the manubrium of malleus and the actuator end piece in the implanted state of the ossicular prosthesis, such that the insertion projection extends away from the longitudinal axis of the long process of incus, the manubrium of malleus, or the actuator end piece, respectively.

9. The ossicular prosthesis according to claim 1, wherein the elongated perforations in the bight are produced by laser cutting.

10. The ossicular prosthesis according to claim 1, wherein the second coupling element is designed as a piston for engagement in the inner ear.

11. The ossicular prosthesis according to claim 1, wherein the ossicular prosthesis is composed entirely or partially of a material having memory effect, superelastic properties or both.

12. The ossicular prosthesis according to claim 11, wherein the material is made of Nitinol.

13. The ossicular prosthesis according to claim 1, wherein the prosthesis body comprises at least one joint, more particularly a ball joint.

* * * * *